United States Patent
Carney et al.

(10) Patent No.: US 7,671,297 B2
(45) Date of Patent: Mar. 2, 2010

(54) METHOD AND APPARATUS FOR LASER DRILLING WORKPIECES

(75) Inventors: R. Christopher Carney, Clinton, NJ (US); David Demarest, Parsippany, NJ (US); Reza K. Mozavi, Alto, GA (US); Angel Perez, Dacula, GA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/718,122

(22) Filed: Nov. 20, 2003

(65) Prior Publication Data
US 2005/0109741 A1    May 26, 2005

(51) Int. Cl.
    B23K 26/00    (2006.01)
(52) U.S. Cl. .................... 219/121.71; 219/121.7
(58) Field of Classification Search ........... 219/121.71, 219/121.7, 121.85, 121.65, 121.66, 121.69, 219/121.67, 121.68
    See application file for complete search history.

(56) References Cited

U.S. PATENT DOCUMENTS

| | | | | |
|---|---|---|---|---|
| 2,496,051 | A * | 1/1950 | Hillier | 250/398 |
| 4,201,905 | A * | 5/1980 | Clark et al. | 219/121.6 |
| 4,581,939 | A * | 4/1986 | Takahashi | 73/643 |
| 4,726,645 | A * | 2/1988 | Yamashita et al. | 385/35 |
| 4,960,970 | A * | 10/1990 | Schneiter | 219/121.6 |
| 5,045,669 | A * | 9/1991 | Ortiz et al. | 219/121.83 |
| 5,207,673 | A * | 5/1993 | Ebling et al. | 606/16 |
| 5,322,589 | A * | 6/1994 | Matsuoka et al. | 438/479 |
| 6,252,195 | B1 * | 6/2001 | Mosavi et al. | 219/121.69 |
| 6,341,029 | B1 * | 1/2002 | Fillion et al. | 359/212 |
| 6,720,567 | B2 * | 4/2004 | Fordahl et al. | 250/559.29 |
| 6,828,524 | B2 * | 12/2004 | Hong et al. | 219/121.6 |
| 2003/0000930 | A1 * | 1/2003 | Hamada | 219/121.73 |
| 2003/0132208 | A1 * | 7/2003 | Cutler | 219/121.72 |

FOREIGN PATENT DOCUMENTS

| | | | |
|---|---|---|---|
| DE | 3938779 A1 | * | 5/1991 |
| JP | 01-215290 | * | 8/1989 |
| JP | 3-124385 | * | 5/1991 |

* cited by examiner

*Primary Examiner*—M. Alexandra Elve
(74) *Attorney, Agent, or Firm*—Nutter McClennen & Fish LLP

(57) ABSTRACT

A method and apparatus for laser drilling a vibrating workpiece. A laser is mounted to a stationary frame. A separate machine having a separate machine frame has a spherical lens mounted to the top of the machine frame in proximity to a workpiece engaged by the machine. The vibrations of the machine caused by operation are transmitted to the lens and workpiece. A laser beam emitted by the laser is transmitted thought the lens and focused on the workpiece. The apparatus and method provides for precisely drilled and located holes or openings in the workpiece.

8 Claims, 3 Drawing Sheets

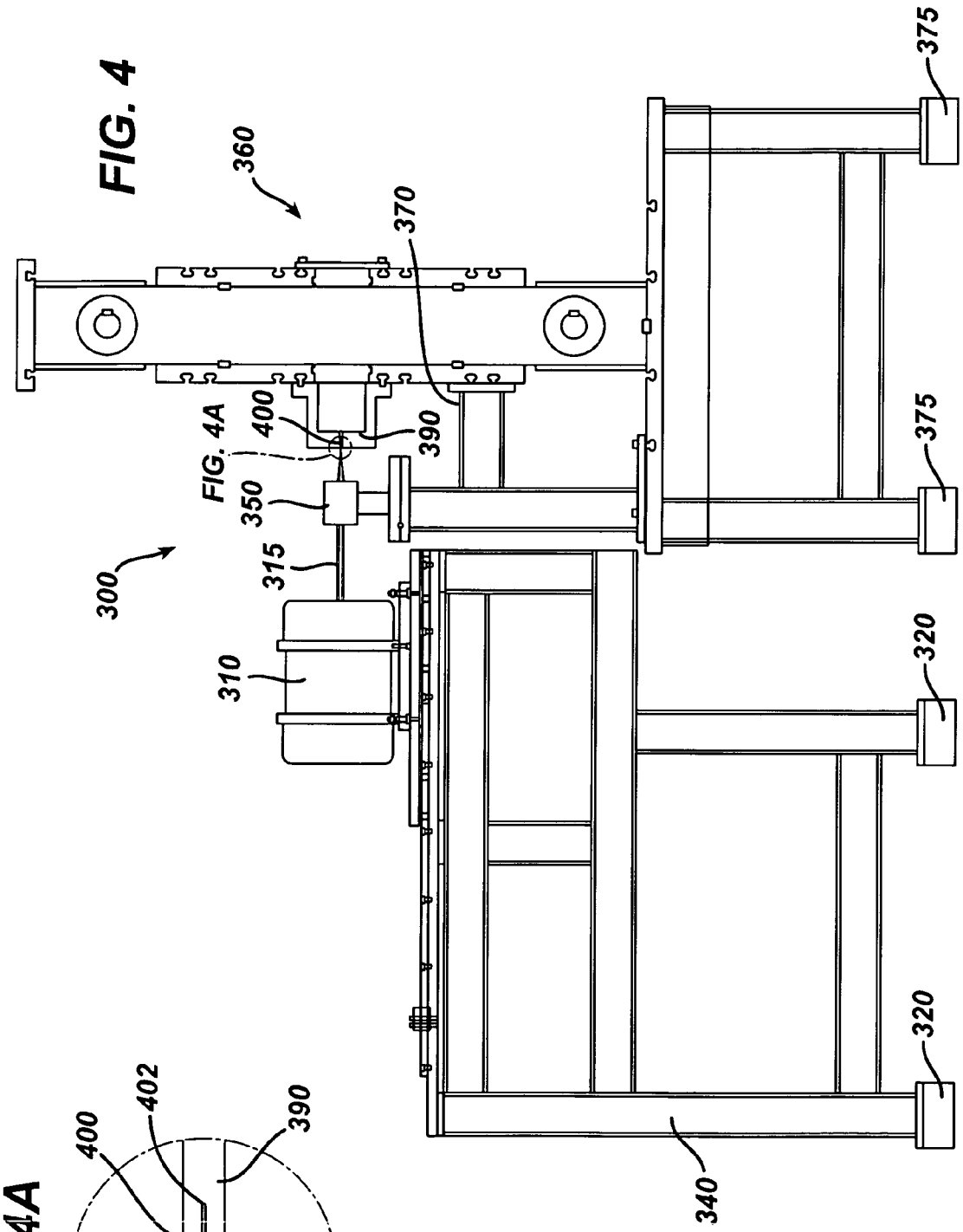

METHOD AND APPARATUS FOR LASER DRILLING WORKPIECES

TECHNICAL FIELD

The field of art to which this invention pertains is laser drilling, more specifically, laser drilling of workpieces.

BACKGROUND OF THE INVENTION

Laser drilling apparatuses and methods of drilling work pieces or objects are well known in the art. For example, it is known to use lasers and associated optics to drill holes in surgical needles, medical devices, aerospace components, automotive components, electronic components, and military components. The size of the opening to be drilled in the workpiece, and the type of material will dictate the type of laser and its output. Types of lasers that can be used for drilling procedures include Nd-Yag, carbon dioxide, and ruby lasers. Power outputs of these lasers may typically be in the hundreds of watts and are a function of the materials, hole diameters, hole depths, and beam energy required to drill such holes.

When drilling a hole in a metal workpiece, it is known that the metal heated by the laser beam is melted in discrete volumetric sections as the heat from the laser beam is absorbed and conducted by the metal. The molten metal subsequently is expelled from the opening by the force of vaporized metal that is also produced by the laser beam. In order to efficiently produce an opening and a hole in a metal work piece using a laser drilling apparatus, it is typically necessary to pulse the laser beam in precise, timed segments to allow the volumes of molten metal to be expelled as each laser beam segment is applied.

Quite often, laser drilling operations are conducted in high speed manufacturing environments where the workpieces are mounted to high speed production machines, such as progressive index machines. Inherent with such operations and machinery is vibration that is transmitted through the machinery and to the workpiece. This can be problematic if the hole to be drilled in the workpiece must be precisely located and must have precise dimensions. It is known to mount lasers to the frames of high speed machinery on vibration absorbing mounts, but this typically will not eliminate all of the vibration to the laser, and the workpiece continues to vibrate. It is known that the mirrors and other components of a laser are sensitive and can become misaligned or damaged by vibration. Similarly, it is know to mount a laser remotely from the frame of the high speed machine. Although this protects the laser from vibration, it does not eliminate the problems associated with the workpiece vibrating and does not alleviate the difficulties in attempting to precisely drill a hole in the workpiece.

Therefore, there is a need in this art for a novel method of laser drilling workpieces, along with novel apparatuses, that allows vibrating workpieces to be drilled precisely.

SUMMARY OF THE INVENTION

Accordingly, a novel laser drilling process is disclosed. A workpiece mounted to a vibrating frame is provided, wherein both the workpiece and the frame vibrate in unison. A laser is mounted to a second frame. The second frame is substantially isolated from the vibrating frame. A spherical focusing lens is rigidly mounted to the first vibrating frame such that a beam emitted from the laser is in substantial alignment with the vibrating workpiece. A laser beam is emitted from laser and directed through the spherical lens onto a target site on the workpiece.

Another aspect of the present invention is an apparatus for laser drilling a vibrating workpiece. The apparatus has a laser mounted to a first frame. A spherical focusing lens is rigidly mounted to a second frame of a vibrating machine. A workpiece is engaged by the machine. The laser and lens are aligned to provide a focused beam at a target site on the workpiece.

These and other aspects and advantages of the present invention will become more apparent from the following description and accompanying drawings.

BRIEF DESCRIPTION OF THE DRAWINGS

FIG. 4 illustrates a laser drilling apparatus of the present invention.

FIG. 4A is a partial, magnified view of the needle and fixture of FIG. 4.

DETAILED DESCRIPTION OF THE INVENTION

The lasers that can be used in the method and apparatus include conventional lasers such as Nd-YAG lasers, carbon dioxide lasers, ruby lasers and the like. A particularly preferred laser is Nd-Yag. The power of the lasers will be sufficient to provide effective drilling of a hole in a workpiece. This will be dependent upon a number of factors including the size and depth of the hole, the type of material, the drilling time, beam size, beam amplification, pulse width, number of pulses, environment and the like. When drilling suture mounting bore holes in stainless steel surgical needles, for example, the average beam power will typically range from 10 watts to about 500 watts. In addition, a controlled pulsing system is used to control the laser beam. It is necessary to pulse a laser in a metal drilling operation because the pulse train allows control of hole shape and quality as well as hole size, and to some degree depth. The pulse train allows control of the drilling process to optimize the peak and average laser power used to drill the workpiece. Pulsed laser drilling systems are described in U.S. Pat. No. 6,252,195 which is incorporated by reference.

The spherical lenses that can be used in the methods and apparatus of the present invention will have sufficient optical characteristics to effectively focus a laser beam onto a target site on a vibrating workpiece. To minimize the effects of spherical aberrations the focal lens must take into consideration laser beam diameter, lens size, and static beam alignment.

Figure 1:
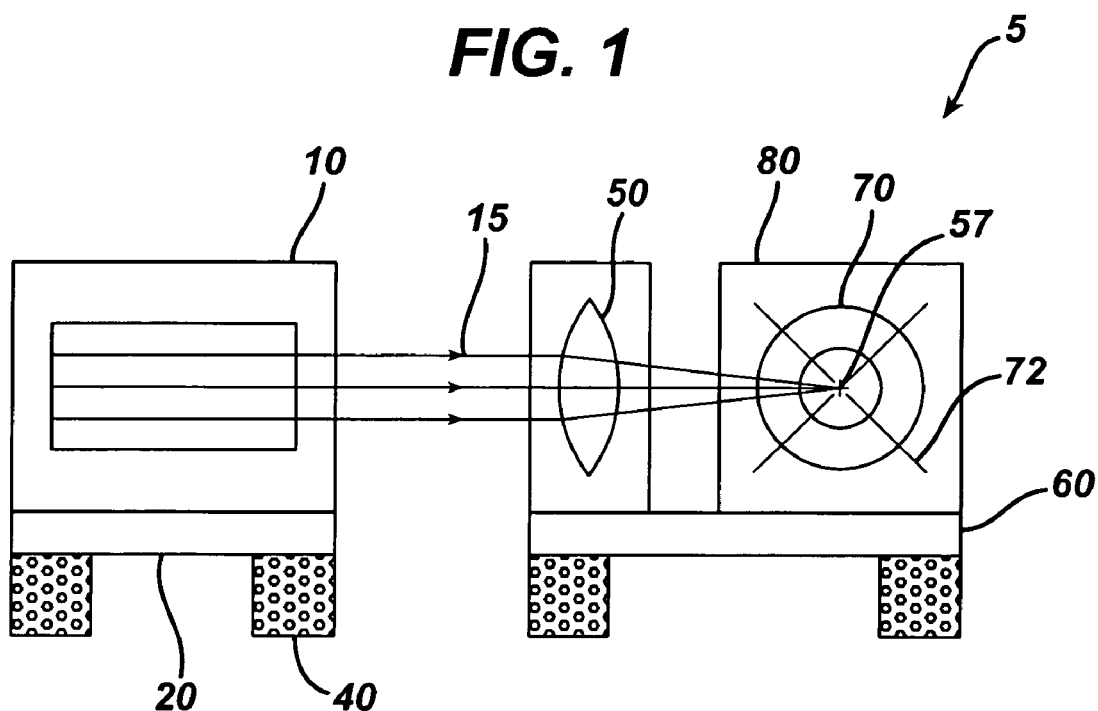
FIG. 1 is a schematic of a laser apparatus of the present invention used for laser drilling a vibrating workpiece.

A schematic of a laser drilling apparatus 5 of the present invention is seen in FIG. 1. The laser 10 is mounted to a table 20. The laser 10 is seen to be mounted to conventional vibration pads 40. The spherical lens 50 is seen to be mounted to machine frame 60 in proximity to workpiece 70. As used generally herein, what is meant by mounted to the machine frame is that the workpiece is either mounted directly to the machine frame or may be mounted in a conventional fixture device that is in turn mounted to the machine frame. In either case, the workpiece would vibrate in unison with the fixture and/or machine frame. Workpiece 70 is engaged by a conventional progressive tooled production machine 80. Lens 50 is rigidly mounted to the machine frame 60. A laser light beam 15 emitted by laser 10 is seen to travel through spherical lens 50 and to be collimated and focused at focal point 57 which corresponds spatially to a target site 72 on workpiece 70. As machine frame 60 vibrates, the workpiece 70 and the lens 50 vibrate in a substantially synchronous manner. At the same time, laser 10 and laser beam 15 are substantially fixed spatially with respect to the vibrating workpiece 70 and lens 50. Because of the physics of a spherical lens, as long as the vibratory movement of the lens 50 is substantially perpendicular or axial to the laser beam 15, and thus the laser beam 15 enters the lens 50 on a path parallel to the central axis of the lens 50, the beam 15 will be focused at the same target site 72 on workpiece and at focal point 57. This results in ability of the laser system to drill precise holes in precise location on and in a vibrating workpiece. In addition, the laser 10 is not subjected to vibratory forces which can result in a variety of problems and damage to the laser such as misalignment of the mirrors, prisms, beam expanders, crystals and the like.

Figure 2:
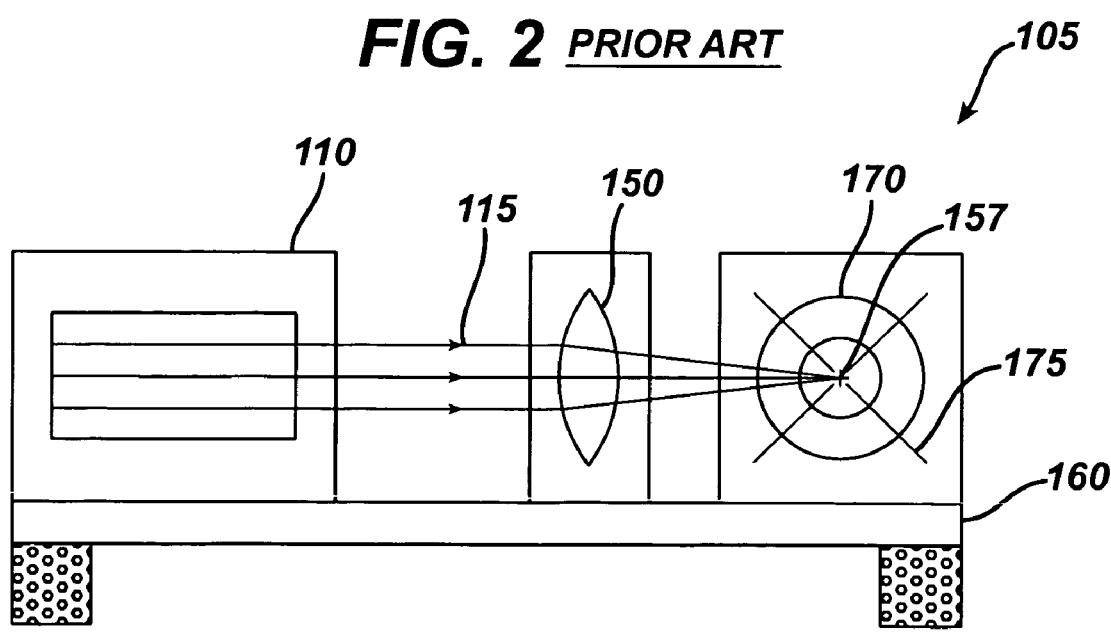
FIG. 2 is a schematic of a laser drilling apparatus of the prior art wherein the laser and focal lens are mounted to the machine to which the workpiece is engaged.

A standard configuration 105 known in the art for laser drilling workpieces on a vibrating high speed machine is seen in FIG. 2. The laser 110 and lens 150 are both mounted to the vibrating machine frame 160. A workpiece 170 having a target site 175 is engaged in proximity to the lens 150 by clamp tooling. A laser beam 115 is directed through spherical lens 150 such that it is collimated at focal point 157, which corresponds spatially to target site 175. In this configuration, the laser 110, the lens 150 and the workpiece 170 are all conducting vibrations transmitted through the machine frame 160. The problems associated with this prior art approach to laser drilling include laser damage, laser alignment damage, variations in targeting.

Figure 3:
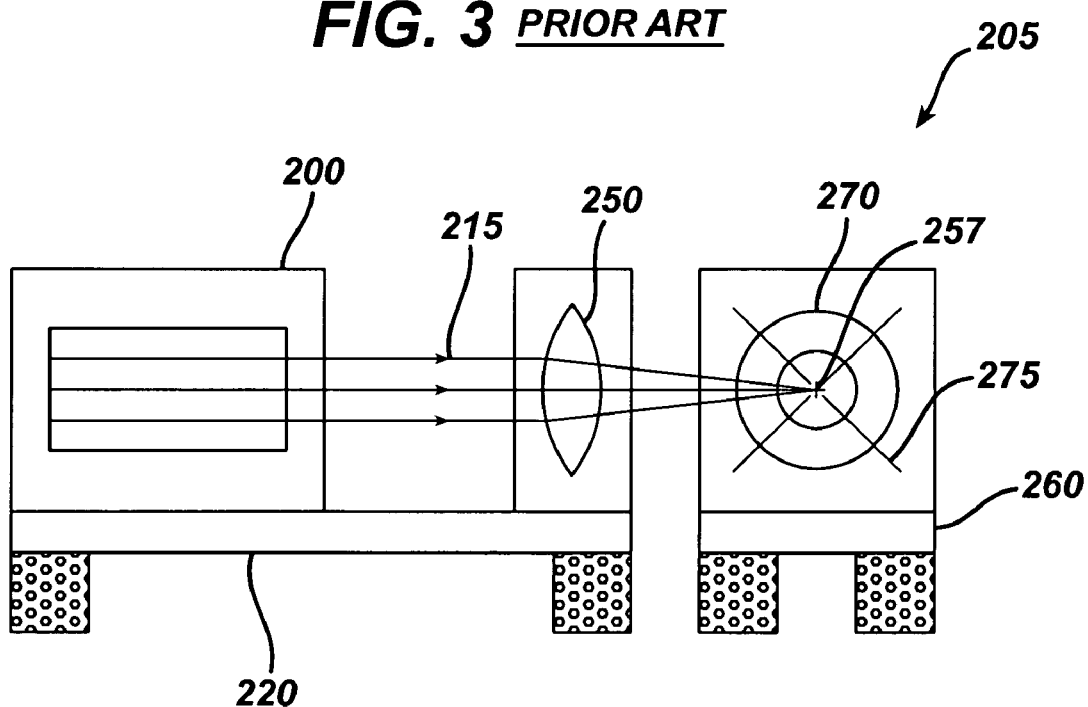
FIG. 3 is a schematic of a laser drilling apparatus of the prior art used for drilling a vibrating workpiece, wherein the laser and a focusing lens are mounted to a separate frame that is separate from the machine frame to which the workpiece is engaged.

Another known configuration 205 for laser drilling workpieces is illustrated in FIG. 3. As seen in FIG. 3, the laser 200 and the lens 250 are mounted on a separate, stationary frame 220. The workpiece 270 is engaged on vibrating machine frame 260. Vibration of machine frame 260 will cause vibration to be transmitted to workpiece 270 causing it to displace with respect to laser bean 215 emitted by laser 200. This in turn will cause the focal point 257 of lens 250 to move with respect to the target site 275 on workpiece 270 causing deficiencies in both the location and dimensional preciseness of the drilled hole.

FIG. 4 illustrates a preferred embodiment of a laser drilling apparatus 300 of the present invention. The laser 310 is mounted to a separate, stationary frame 340. Laser 310 is mounted on conventional vibration pads 320. The lens 350 is seen to be mounted to machine frame 370 of conventional progressive manufacturing machine 360 having vibration mounts 375. A conventional surgical needle 400 is seen to be engaged by conventional workpiece-holding fixture 390. Surgical needle 400 has distal pointed piercing end 402 and proximal end 404. Surgical needle 400, machine frame 370 and fixture 390 vibrate substantially in unison. A laser beam 315 is seen to directed through lens 350 onto the proximal end 404 of needle 400 onto target site 410 to drill a suture-mounting hole.

The laser drilling apparatus and the drilling method of the present invention have many advantages. The advantages include increased life of laser and optical beam alignment leading to increased quality of laser beam. Increased precision of focal point on target leading to less variation in final hole position.

Although this invention has been shown and described with respect to detailed embodiments thereof, it will be understood by those skilled in the art that various changes in form and detail thereof may be made without departing from the spirit and scope of the claimed invention.

We claim:

1. A method of laser drilling a vibrating workpiece, comprising:
   providing a workpiece engaged by a first vibrating frame of a vibrating machine, wherein the workpiece is vibrating substantially in unison with the first vibrating frame;
   providing a laser apparatus mounted to a second frame, wherein the second frame is substantially isolated from the vibrating frame and does not vibrate;
   providing a spherical focusing lens that is mounted to the first vibrating frame, wherein the spherical focusing lens is vibrating substantially in unison with the first vibrating frame;
   aligning the laser apparatus and the spherical focusing lens such that a laser beam emitted by the laser apparatus is directed through the vibrating spherical focusing lens to a target location on the vibrating workpiece; and
   causing the laser apparatus to emit a beam through the spherical focusing lens, wherein the beam is stationary with respect to the vibrating spherical focusing lens, and wherein the beam strikes the vibrating workpiece at the target location.

2. The method of claim 1, wherein the laser comprises an Nd-Yag laser.

3. The method of claim 1, wherein the workpiece comprises a surgical needle.

4. The method of claim 1, wherein the laser beam is pulsed.

5. The method of claim 1, wherein the workpiece is mounted to a fixture which is mounted to the first vibrating frame, wherein the fixture vibrates substantially in unison with the first vibrating frame.

6. An apparatus for laser drilling a vibrating workpiece, comprising:
   a workpiece mounted to a first vibrating frame;
   a laser apparatus mounted to a second frame, wherein the second frame is substantially isolated from the first vibrating frame and is substantially non-vibrating; and,
   a spherical focusing lens mounted to the first vibrating frame for directing a laser beam emitted by the laser apparatus to a target site on the workpiece, such that the spherical focusing lens vibrates substantially in unison with the first vibrating frame, while the laser beam is substantially stationary with respect to the vibrating spherical focusing lens.

7. The apparatus of claim 6, wherein the laser comprises an Nd-Yag laser.

8. The apparatus of claim 6 wherein the workpiece comprises a surgical needle.

* * * * *